(12) United States Patent
Schmidt et al.

(10) Patent No.: US 6,659,992 B1
(45) Date of Patent: Dec. 9, 2003

(54) ABSORBENT ARTICLE INSTANTEOUSLY STORING LIQUID IN A PREDEFINED PATTERN

(75) Inventors: Mattias Schmidt, Idstein (DE); Bruno Johannes Ehrnsperger, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,224

(22) PCT Filed: Jun. 29, 1999

(86) PCT No.: PCT/US99/14646

§ 371 (c)(1),
(2), (4) Date: Dec. 20, 2000

(87) PCT Pub. No.: WO00/00140

PCT Pub. Date: Jan. 6, 2000

(30) Foreign Application Priority Data

| Jun. 29, 1998 | (WO) | PCT/US98/13449 |
| Jun. 29, 1998 | (WO) | PCT/US98/13497 |
| Jun. 29, 1998 | (WO) | PCT/US98/13521 |
| Jun. 29, 1998 | (WO) | PCT/US98/13523 |

(51) Int. Cl.$^7$ ................................................. A61F 13/15
(52) U.S. Cl. ................................................. 604/385.101
(58) Field of Search ........................... 604/378, 385.101

(56) References Cited

U.S. PATENT DOCUMENTS 5,562,646 A    10/1996   Goldman et al.
5,599,335 A    2/1997    Goldman et al.

FOREIGN PATENT DOCUMENTS

| EP | 0 399 564 A2 | 11/1990 |
| WO | WO 94/13704 | 6/1994 |
| WO | WO 98/22065 | 5/1998 |
| WO | WO 98/22067 | * 5/1998 |
| WO | WO 98/43578 | 10/1998 |
| WO | WO 99/55264 | 11/1999 |
| WO | WO 00/00129 | 1/2000 |
| WO | WO 00/00136 | 1/2000 |
| WO | WO 00/00138 | 1/2000 |
| WO | WO 00/00143 | 1/2000 |
| WO | WO 00/00146 | 1/2000 |

* cited by examiner

Primary Examiner—Dennis Ruhl
(74) Attorney, Agent, or Firm—Eileen L. Hughett; Edward J. Milbrada; Ken K. Patel

(57) ABSTRACT

An absorbent article such as a diaper, a training pant, an adult incontinence article, a bed mate, or the like is capable of rapidly transporting urine away from its acquisition zone. In particular the absorbent article stores a fraction of the acquired liquid outside of its acquisition region which fraction remains relatively unchanged between 20 percent and 100 percent load of the article. A process for handling urine in the absorbent article comprises a step of transporting a relatively constant fraction of the acquired liquid away from the acquisition zone of the article.

8 Claims, No Drawings

ABSORBENT ARTICLE INSTANTEOUSLY STORING LIQUID IN A PREDEFINED PATTERN

FIELD OF THE INVENTION

The present invention relates to absorbent articles such as diapers, training pants, adult incontinence articles, bed mats, and the like. In particular, the present invention relates to those absorbent articles which store urine by means of either capillary or osmotic pressure.

BACKGROUND

Absorbent articles such as diapers, training pants, adult incontinence articles, bed mats, and the like are well known in the art and are frequently used for example for babies, toddlers, incontinent persons, and bed-ridden persons.

It has been recognized in the prior art that storage of acquired urine close to the respective body exit may bear inherent disadvantages. The human urethra is located almost in between the legs of the human being. Hence, storage in particular of larger amounts of urine close to the urethra would lead to increased bulk in between the legs of the wearer. Increased bulk, of course, limits the mobility of the wearer and thus is uncomfortable. It is therefore desirable to store the acquired urine away from the point of acquisition.

Liquid distribution away from the point of acquisition also has further advantages. Since a larger area may be used for storage of the acquired urine away from the point of acquisition, the caliper of the storage area as a whole may be reduced. Hence, the article for handling body urine which comprises the storage member appears less bulky.

PCT patent publication WO 98/22067 (Matthews et al.) provides a personal care product in which the ratio of the amount of liquid stored in the center region to the amount of liquid storage in at least one of the end regions 30 minutes after an insult is less than 5:1. This prior art, however, fails to provide an absorbent article which transports a larger amount of urine away from the acquisition region. In addition, it fails to provide a sufficiently rapid liquid transportation away from the acquisition region.

PCT patent application WO 98/43578 (LaVon et al.) provides an absorbent article comprising absorbent core with a crotch region and at least one waist region whereby said crotch region has a lower ultimate liquid storage capability than the waist region. The article further has an improved liquid handling performance such as an acquisition rate of at least 0.6 milliliters per second in the fourth gush.

Hence, it is an object of the present invention to overcome the problems of the prior art absorbent articles.

It is a further object of the present invention to provide an absorbent article which transports urine away from the acquisition region immediately after acquisition of the urine.

Is a further object of the present invention to provide an absorbent article which stores a substantial amount of urine outside the acquisition region.

SUMMARY OF THE INVENTION

The present invention further provides an absorbent article comprising an acquisition region, a waist region separate from said acquisition region. The absorbent article is characterized in that the article has a fill pattern difference of less than 30% according to the Instantaneous Storage Pattern test method defined herein.

The present invention further provides a process for handling urine in an absorbent article, the article comprising an acquisition region and at least one waist region being separate from said acquisition region. The process for handling urine comprising the steps of:

acquiring liquid into said article at said acquisition region, the amount of said liquid being a fraction A of the total design capacity of the article;

transporting a fraction B of said acquired liquid to at least one of said waist regions, said fraction B being at least 20%.

The process of the present invention is characterized in that for any value of said fraction A between 20% and 100% said fraction B differs by less than 30% from the value of fraction B for a fraction A of 20%.

DETAILED DESCRIPTION OF THE INVENTION

The present invention is described in the following by means of a variety of different embodiments and by means of a variety of different features. Further embodiments of the present invention may be obtained by combining features of one embodiment with features of another embodiment disclosed herein and/or with other features disclosed herein. These further embodiments are considered to be implicitly disclosed herein and hence form part of the present invention. It will be apparent to the skilled person that combinations of certain features may lead to non-functional articles not forming part of this present invention.

It is one aspect of the present invention to provide an article for managing urine. It is another aspect of the present invention to provide a process for storing urine in an article for managing urine in a instantaneous fill pattern.

The absorbent article of the present invention is capable of rapidly distributing the acquired urine away from its acquisition region to at least one of its waist regions. For the purpose of this invention, this capability is quantified by the Instantaneous Storage Pattern Test method defined hereinafter. According to this test, the absorbent article according to the present invention has a fill pattern difference of less than 30 percent, preferably a fill pattern difference of less than 20 percent, more preferably a fill pattern difference of less than 10 percent, most preferably a fill pattern difference of less than 5 percent.

Preferably, the absorbent article of the present invention further rapidly acquires urine in an in-use configuration. For the purposes of the present invention, this capability is quantified by the curved acquisition test disclosed hereinafter. The absorbent article according to the present invention has a liquid acquisition rate in the fourth gush of at least 2 milliliters per second, preferably a liquid acquisition rate in the fourth gush of at least 2.5 milliliters per second, more preferably a liquid acquisition rate in the fourth gush of at least 3 milliliters per second, most preferably a liquid acquisition rate in the fourth gush of at least 4 milliliters per second.

The entire absorbent article of the present invention is intended to be worn by a wearer such that the wearer retains his mobility during use of the article of the present invention. In some embodiments of the present invention, the absorbent article of the present invention comprises an attachment means which is unitary with the article. The term "unitary" as used herein indicates that the attachment means is joined to the absorbent article and that the attachment means is not intended to be separated from the article during use of the article. The attachment means is intended to hold the absorbent article of the present invention around the lower torso of the wearer during use. Suitable attachment means such as for example adhesive tapes, mechanical fasteners, garment like articles, and the like are well known in the art. Alternatively, the absorbent article of the present invention may be attached to the lower torso of the wearer by an attachment means which is not unitary with the article such as for example a pant.

It is further desirable for the absorbent article of the present invention that it is sufficiently flexible to readily conform with the body of the wearer during use.

For the purpose of the present invention, a Cartesian coordinate system is defined as follows. The z-direction is defined to be perpendicular to the surface of the acquisition region at the intended loading point. The x-direction is defined to coincide with the longitudinal dimension of the absorbent article. In the case of a diaper, the x-direction runs from the front region of the article (which comes into contact the front waist region of the wearer during use) to the back region of the article (which comes into contact with a back waist region of the wearer during use). Accordingly, the y-direction coincides with a transverse dimension of the absorbent article which runs from the left to the right of the wearer during use. It is to be understood in this context that this Cartesian coordinate system is only a truly Cartesian coordinate system when the article is in the flat out configuration. For typical in use conditions, the configuration of the article is such that x-, y-, and z-direction as defined above only form a locally perpendicular set of coordinates.

The term "instantaneous fill pattern" as used herein refers to a loading distribution between the acquisition region and the waist region of the article that is present already at loadings which are small compared to the total capacity of the article and that is present on a time scale short compared to the average time interval between subsequent gushes.

The article of the present invention has a total design capacity. The term "total design capacity" as used herein refers to the maximum volume of urine that the article is designed to absorb. Typically, the total design capacity equals the combined capacity of all storage members under typical usage conditions. If the storage members can not be identified, then the total design capacity may be determined by the Capacity Dunk Test defined hereinafter. The total design capacity is also related to the amount of urine exudates by the user of the article during the intended usage period. Some articles according to the present invention may be designed to have replaceable storage members. In this case, the total design capacity is related to the capacity of a single storage member or a single set of storage members.

The article for managing urine of the present invention comprises at least one acquisition region. The term "acquisition region" as used herein refers to that region of the article which comprises the intended loading point of the article. The term "loading point" as used herein is that point or region of the article which is intended to be positioned closest to the exit of the urethra of the wearer during use. Typically, the acquisition region is dimensioned such that it allows for variation of the mutual relative positioning of the respective body exit with respect to the article. The acquisition region may also comprise means for intermediate storage of the acquired liquids. Generally, the acquisition region extends over at least a third of the longitudinal dimension of the absorbent article (typically one third), extends over the entire transverse dimension of the absorbent article, and extends over the entire caliper of the absorbent article. Further, the acquisition region is positioned within the absorbent article such that the intended loading point is centered with respect to the acquisition region.

The article for managing urine of the present invention comprises at least one waist region. The term "waist region" as used herein refers to those regions forward and/or backward of the above mentioned acquisition region of the absorbent article. Accordingly, the waist regions may account for up to two thirds of the longitudinal dimension (x-direction) of the absorbent article. Like the acquisition region, the waist region extends over the entire transverse dimension of the absorbent article and extends over the entire caliper of the absorbent article. The waist regions are typically intended to be positioned in close proximity to the front waist region or the back waist region respectively of the wearer during use.

It is to be understood in this context that these regions are defined in a purely geometric way. In particular, there is no need that the positioning of these regions is reflected in the structure of the article such as by a change in material.

In at least one of these waist regions, at least one liquid storage member may be positioned. The intention of the liquid storage member is to ultimately hold the liquid until the end of the intended usage period. In one embodiment of the present invention, the storage member holds the urine by a means selected from the group of capillary pressure and osmotic pressure. For example, the storage member may comprise a pad of cellulosic fibers and optionally a particulate superabsorbent polymeric material dispersed therein. Other suitable storage member include but are not limited to HIPE foams, superabsorbent fibers, and the like. Yet other suitable storage members are well known in the art.

Optionally, the absorbent article according to the present invention may comprise a liquid handling member which is intended to transport urine from the acquisition region to a waist region and potentially to a storage member positioned inside a waist region.

The process for handling urine according to the present invention comprises a step of acquiring urine into the article of the present invention at the acquisition region of the article. Typically, the step is triggered by the disposal of urine onto the acquisition region of the article by the wearer. Preferably, the acquisition rate of the article during the step is sufficiently high to minimize liquid runoff from the article which subsequently may lead to leakage and to minimize skin contact with the urine. During this acquisition step, a certain volume of urine is acquired into the article which is a fraction A of the total design capacity of the absorbent article.

The process for handling urine according to the present invention comprises a step of transporting urine away from the acquisition region to at least one of the waist regions. The urine may be further transported into at least one storage member positioned in at least one of the waist regions. During the step of transportation a fraction B of the acquired liquid is transported away from the acquisition region into at least one of the waist regions. Fraction B is at least 20 percent, preferably at least 50 percent, more preferably at least 75 percent, most preferably at least 95 percent.

During the process of the present invention, fraction B remains relatively unchanged for a wide range of loads of the absorbent article. Thus, even small loads of urine would already be distributed away from the acquisition region of the article and will not contribute to the bulk of the acquisition region. For any value of fraction A between 20 percent and 100 percent, the value of fraction B differs by less than 30 percent from the value of fraction B for a fraction A of 20 percent, preferably by less than 20 percent, more preferably by less than 10 percent and most preferably by less than 5 percent. In other words, the instantaneous loading pattern which stores a fraction B of the acquired liquid away from the acquisition region will remain constant up to the full load of the absorbent article. Preferably, the value of fraction B remains unchanged also for values of fraction A lower than 20 percent and particularly down to 5 percent.

Optionally, the step of transporting liquid away from the acquisition region may be carried out substantially immediately subsequent to the step of acquiring liquid into the absorbent article. Hence, the acquisition region is only bulky for a shorter period of time and may be ready earlier for the acquisition of additional gushes of liquid.

Optionally, the step of transporting liquid away from the acquisition region may be carried out by an optional liquid handling member of the present invention.

It is a further aspect of the present invention to provide a process for handling urine for incontinent person of all ages. This process a step of attaching the absorbent article to the lower torso of the wearer. During the step, the attachment of the article is achieved by means of a suitable attachment means. The attachment means be unitary with the article or may non-unitary with the article. The step may be carried out by the wearer himself or the step may be carried out by a caregiver. The purpose of the step is to align urethra with the acquisition region of the article. The process for handling urine for incontinent persons further comprises the steps of the process for handling urine in an absorbent article according to of the present invention.

In the following, a suitable embodiment of the liquid handling member will be described. The liquid handling member is assembled from an open celled foam material which is completely enveloped by a membrane. A suitable membrane material is available from SEFAR of Rüschlikon, Switzerland, under the designation SEFAR 03-20/14. A suitable foam material is available from Recticel of Brussels, Belgium, under the designation Bulpren S10 black. A suitable technique to completely envelope the foam material with the membrane material is to wrap the membrane material around the foam material and to subsequently heat seal all open edges of the membrane material. It will be readily apparent to the skilled practitioner to choose other similarly suitable materials. Depending on the specific intended application of the liquid handling member, it may also be required to choose similar materials with slightly different properties. After assembly, the liquid handling member is activated by immersing the liquid handling member in water or in synthetic urine until the liquid handling member is completely filled with liquid and until the membranes are completely wetted with liquid. After activation, a part of the liquid inside the liquid handling member may be squeezed out by applying an external pressure to the liquid handling member. If the activation of the liquid handling member was successful, the liquid handling member should not suck air through the membranes.

The particular geometry of the liquid handling member of the present invention can be varied to according to the specific requirements off the intended application. If, for example, the liquid handling member is intended to be used in an absorbent article the liquid handling member may be defined such that its zone of intended liquid acquisition fits between the legs of the wearer and further that its intended liquid discharge zone matches the form of the storage member associated to it. Accordingly, the outer dimensions of the liquid handling member such as length, width, or thickness may also be adapted to the specific needs of the intended application. In this context, it has to be understood , however, that the design of the outer form of the liquid handling member may have an impact on its performance. For example, the cross section of the liquid handling member directly impacts on its flow rate.

For application of the liquid handling member in an absorbent article according to the present invention, the liquid handling member is combined with a storage member. The term "liquid storage member" refers to an article which is capable of acquiring and storing liquid. The volume of the liquid storage member may vary with the amount of stored liquid such as by swelling. Typically, the storage member will imbibe the liquid by means of capillary suction and/or osmotic pressure. Other storage members may also use vacuum as a means to store the liquid. The liquid storage member is further capable of holding at least a portion of the stored liquid under pressure. Suitable storage members are well known in the art and may comprise for example a super absorbent polymeric material such as polyacrylate. The storage member may further comprise a fibrous structure, such as a pad of cellulosic fibers, in which the particulate superabsorbent material is dispersed. In order to pick up the liquid discharged from the liquid handling member, the storage member may be placed in direct liquid communication with the intended liquid discharge zone of the liquid handling member. A suitable storage member is for example a superabsorbent polymer such as available from CHEMDAL, United Kingdom, under the designation ASAP400.

Further examples of suitable superabsorbent polymers, often also referred to as "hydrogel forming polymer" or "absorbent gelling material", are described in U.S. Pat. No. 5,562,646 (Goldman et al.), issued Oct. 8, 1996 and U.S. Pat. No. 5,599,335 (Goldman et al.), issued Feb. 4, 1997.

Other liquid handling members suitable for the purposes of the present invention are described for example in the PCT patent application No. PCT/US98/13497 entitled "Liquid transport member for high flux rates between two port regions" filed in the name of Ehrnsperger et al. filed on Jun. 29, 1998, and in the following PCT patent applications co-filed with the present application entitled "High flux liquid transport members comprising two different permeability regions" (P&G case CM1840MQ) filed in the name of Ehrnsperger et al., "Liquid transport member for high flux rates between two port regions" (P&G case CM1841MQ) filed in the name of Ehrnsperger et al., "Liquid transport member for high flux rates against gravity" (P&G case CM1842MQ) filed in the name of Ehrnsperger et al., "Liquid transport member having high permeability bulk regions and high bubble point pressure port regions" (P&G case CM1843MQ) filed in the name of Ehrnsperger et al. All of these documents are enclosed herein by reference.

In one embodiment of the present invention, the liquid handling member of the present invention is geometrically saturated or substantially geometrically saturated with free liquid. The term "free liquid" as used herein refers to liquid which is not bound to a specific surface or other entity. Free liquid can be distinguished from bound liquid by measuring the proton spin relaxation time $T_2$ of the liquid molecules a according to NMR (nuclear magnetic resonance) spectroscopy methods well known in the art.

The term "geometrically saturated" as used herein refers to a region of a porous material in which the liquid accessible void spaces have been filled with a liquid. The void spaces referred to in this definition are those which are present in the current geometric configuration of the porous material. In other words, a geometrically saturated device may still be able to accept additional liquid by and only by changing its geometric configuration for example by swelling, although all voids of the device are filled with liquid in the current geometric configuration. A device for handling liquids is called geometrically saturated, if all porous materials that are part of the device and intended for liquid handling are geometrically saturated.

The term "porous material" as used herein refers to materials that comprise at least two phases a solid material and a gas or void phase—and optionally a third liquid phase that may be partially or completely filling said void spaces. The porosity of a material is defined as the ratio between the void volume and the total volume of the material, measured when the material is not filled with liquid. Non-limiting examples for porous materials are foams such as polyurethane, HIPE (see for example PCT patent application WO94/13704), superabsorbent foams and the like, fiber assemblies such as meltblown, spunbond, carded, cellulose webs, fiber beds and the like, porous particles such as clay, zeolites, and the like, geometrically structured materials such as tubes, balloons, channel structures etc. Porous materials might absorb liquids even if they are not hydrophilic. The porosity of the materials is therefore not linked to their affinity for the liquid that might be absorbed.

The term "substantially geometrically saturated" as used herein refers to a member in which at least 90% of the macroscopic void volume of the member are geometrically saturated, preferably at least 95% of the macroscopic void volume of the device are geometrically saturated, more preferably 97% of the macroscopic void volume of the device are geometrically saturated, most preferably 99% of the macroscopic void volume of the device are geometrically saturated.

In one embodiment of the present invention, the absorbent article is a disposable absorbent article such as a diaper, a training pant, a sanitary napkin, an adult incontinence article, or the like. Such an absorbent article may further comprise a liquid pervious topsheet, a liquid impervious backsheet at least partially peripherally joined to the topsheet. The absorbent article may further comprise an absorbent core which may serve as a storage member for the urine. Topsheets, backsheet, and absorbent cores suitable for the present invention are well known in the art. In addition, there are numerous additional features known in the art which can be used in combination with the absorbent article of the present invention such as for example closure mechanisms to attach the absorbent article around the lower torso of the wearer.

Methods

Unless stated otherwise, all methods are carried out at ambient conditions, i.e. 32+/−2° Celsius and 30–50% relative humidity.

Unless stated otherwise, the synthetic urine used in the test methods is commonly known as Jayco SynUrine and is available from Jayco Pharmaceuticals Company of Camp Hill, Pa. The formula for the synthetic urine is: 2.0 g/: of KCI; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Capacity Dunk Test

This test is intended to measure the total capacity of an absorbent article.

As the first step of this test, the test specimen is completely immersed in synthetic urine for 10 minutes.

Then, the test specimen is put with its acquisition region facing the glass frit on a sufficiently large glass frit which is in direct liquid communication with a liquid reservoir filled with synthetic urine. Hence, this glass frit provides a hydrohead of about 1mm. After thirty minutes, the test specimen is removed from the glass frit.

Finally, the total capacity of the test specimen is determined by weighing the liquid uptake of the test specimen.

Instantaneous Storage Pattern Test Method

This test method is intended to measure the ratio of the liquid stored outside the acquisition region of an article of the present invention. Therefore, the distribution of stored liquid is measured shortly after the liquid has been acquired at the loading point within the acquisition region. This method is suitable for absorbent articles according to the present invention.

For the purpose of this test method, samples of the article to be tested are loaded with one or more gushes of synthetic urine onto the intended loading point of the article while the article is configured to resemble as closely as possible an in-use configuration. For example, the article may be loaded while it is attached to a mannequin modeling the body shape of an average user or the article may be loaded while the article is held upright in a curved shape. For this test, a gush is defined as having the volume of 20% of the total design capacity of the article to be tested. The gushes are disposed onto the loading point of the article in 5 minute intervals at a rate of about 5 ml/s or at the maximum rate not causing liquid to run-off whichever is lower. The 5 minute interval starts when the preceding gush is completely absorbed by the article.

For the purpose of this test method, the loading or liquid uptake of the acquisition region and the storage regions of the article to be tested have to be measured separately. There exists a variety of potentially suitable test methods to determine the liquid uptake of a certain region. It will be readily apparent to the skilled person which method is the most suitable for the article to be tested. The potentially suitable methods range from very simple methods such as severing the article into its different regions and weighing its weight increase to more complex methods such as x-ray analysis and nuclear magnetic resonance spectroscopy. In x-ray analysis, the effect that the amount of energy absorbed when the article is exposed to x-rays is proportional to the amount of liquid per unit surface area contained in the article is used to determine the water content of specific regions of the article. For example, such a method is described in an article entitled "Fluid distribution: Comparison of x-ray imaging data" by David F. Ring, Oscar Lijap, and Joseph Pascente in Nonwoven World magazine, summer 1995, at pp. 65–70. Suitable x-ray systems are available for example from LIXI Inc. of Downers Grove, Ill. USA, under the designation SA-100-2 SERIES, MODEL HLA-40-440M02. The system uses Bio-scan software from Optimas. The x-ray system may for example be operated with an exposure time of two second, with a tube voltage of 50 kV, and a current of 12 mA. It is to be noted, however, that for exposure time, tube voltage, and current different values have to be chosen depending on the specific properties of the test specimen to be examined. It is also well known in the art to determine the water content of a specific region of a article by nuclear magnetic resonance spectroscopy. In all methods, particular care has to be taken that the weight of the liquid (bound liquid as well as free liquid) which is stored in either one of the regions is exactly accounted for. It is also important that only the liquid uptake is measured by comparing a loaded article with an unloaded article.

The total design capacity of the test specimen may for example be obtained by the Capacity Dunk Test defined herein. The gush size for this test is obtained by dividing the total design capacity of the test specimen by 5.

As a second step, a first sample of the article is loaded with a first gush of synthetic urine at its intended loading point. The loadings of the acquisition region and the storage region of the article are measured five minutes after the gush has been absorbed completely. The loadings will be referred to as $A_1$ and $S_1$ respectively. Then, a second sample of the article to be tested is loaded with 5 subsequent gushes with a 5 minute waiting time between two subsequent gushes. The loadings of the acquisition region and the storage region of the article are measured five minutes after the fifth gush has been absorbed completely. The loadings will be referred to as $A_5$ and $S_5$ respectively.

The fill ratio $R_i$ of a sample of the article loaded with i gushes is the ratio of the loading of the storage region to the loading of the acquisition region and is given by $$R_i = \frac{S_i}{A_i}$$

The fill pattern difference D represents the relative change of the fill ratio from 20% loading to 100% loading. Accordingly, D is obtained by $$D = \frac{|R_5 - R_1|}{R_1}$$

The fill pattern difference should be measured for five pairs of sample articles and subsequently the results should be averaged in order to reduce statistical fluctuation of the results.

Curved Acquisition Method

The curved acquisition test methods aims at simulating the introduction of urine into a device for managing urine. A similar test method is described in PCT patent application No. IB99/00741 (P&G case CM2060FQ) incorporated herein by reference.

The following describes key principles of the test:
1. The device is held in a curved configuration to more realistically simulate the position of the device on a standing or sitting wearer.
2. The realistic, curved configuration requires that the liquid applied must be distributed against gravity.
3. The overall configuration provides key data on acquisition, distribution and storage of the liquid within the various materials thereby providing a better understanding of material properties, and their combined performance.
4. The apparatus includes a pressurized air cushion, allowing to better analyze products which have either a varying thickness throughout various parts thereof, or which exhibit a pronounced thickness change throughout the loading process.

The following description is adopted for devices for handling urine of the baby diaper type, and in particular for devices intended for babies in a weight range of about 9 to 18 kg. Nonetheless, the skilled person will be able to readily adopt it for other purposes, such as for other sizes, or adult incontinence applications. The test specimen is held in a curved plexiglas device which utilizes a flexible, soft air bag which is used to simulate various baby pressures between 0.69 kPa –6.9 kPa (0.1–1 psi), and the test specimen is loaded with subsequent gushes of liquid, with appropriate waiting time in between. The key result from this test is the time for the fluid of each of the gushes to penetrate into the test specimen. After the loading of the test specimen by this test, the test specimen can be used for further analysis, such as measuring the rewet, preferably by the Post Curved Acquisition Collagen Rewet Method (PCACORM) described in PCT patent application IB99/00741 (P&G case CM2060FQ), or measuring the caliper, or measuring the liquid distribution, such as by determining the load in various sections of the test specimen.

For test specimens having the above mentioned size, the standard protocol loads the test specimen four times with 75 ml +/–2 ml, at a rate of 15 ml/sec, delivered at one hour intervals. The present description refers to an automated procedure, including automatic data capturing. Of course, analogous systems can be used, such as manual recording of data, as long as the described principles are followed.

The test equipment is schematically depicted in FIG. 6 of PCT patent application No. IB99/00741 (P&G case CM2060FQ) incorporated herein by reference. The complete equipment, or preferably a multiplicity thereof for ease of replication, is placed inside a controlled condition chamber, with room temperature and humidity within the following limits:

Temperature: 32° C.±2° (90° F.±3° F.)

Relative Humidity: 50%±10%

If a deviation form this protocol is deemed appropriate, this must be stated explicitly in the protocol.

The Curved Acquisition Tester comprises four important parts: (The size of the unit is adapted for baby diapers and may have to be changed accordingly for absorbent article for other intended uses.)

a) A holding unit which is essentially made of perspex/ plexiglas. It has been found that suitable plates of 5 mm thickness provide sufficient strength for operating without undue deformation.

The essential part of the holding unit is a trough having an upper rectangular opening of 130 mm extending outside of the plane of drawing, and a width of 260 mm. The rectangular through has a length of about 200 mm and ends in a semi-cylindrical form having a radius of 130 mm. The holding unit has one or more means to retain the loading unit in place, here shown by a hinged lid and corresponding fixation means, such as screws. The holding unit further comprises means for stable support.

b) A loading unit comprising a liquid application means is designed to fit into the through of the holding unit, by having a rectangular section having a length of about 180 mm, and having cross-section of about 100 mm by 128 mm, ending in a semi-cylindrical section having a radius of 100 mm. The loading unit further comprises a flange, which allows to hang the unit into the trough by being larger than said trough opening, and which also prevents the loading unit to be pushed out of the trough by being hold by said lid. The clearance for the vertical movement of the loading unit is about 4 cm. The total loading unit is made from the same material as the holding unit, and can have a weight of about 1 kg, including the liquid application means.

c) The liquid application means comprises a plexiglas tube having an inner diameter of 47 mm, and a height of about 100 mm. It is firmly affixed to a circular opening having a diameter of about 50 mm through the loading unit, positioned centered around the lowermost point of the semi-cylindrical portion. The opening of the tube is covered by a open mesh (such as of wire mesh with openings of about 2 mm separated by threads of 1 mm), so as to be flush with the opening of the loading unit. A 6 mm diameter flexible tube, such as Norpren A60G (6404-17), available from Cole Parmer Instrument Company, IL, US, is connected to a test fluid metering pump, such as Digital Pump, Catalog, by No. G-07523-20, having a Easy-Load Pump Head, No. G-07518-02, both by Cole-Parmer Instrument Company, IL, US, with a pump control unit to allow start and stop of the pump based upon electrical signals. Two electrodes are positioned at two opposite points just inside the mesh at the lower end of the plexiglas tubing, to be able to detect interruption of the electric current through the electrolyte fluid, once the tube is being emptied. The electrodes are connected via cable to a time signal measuring unit.

d) A pressure generating means comprises a flat, flexible air cushion, such as generally available for medical purposes (blood pressure measurement), having an uninflated dimension of 130 mm by 600 mm, which can be inflated by means of a hand pump and a valve with a pressure recording device, which can be connecting to an electrical transducer so as to provide an electrically recordable signal corresponding to the pressure. This system is designed to operate at pressures of up to 6.89 kPa (1 psi), and is set for the standard procedure to 2.07 kPa (0.3 psi).

e) Optionally, the apparatus can comprise an automatic control unit, such as a suitable computer control unit, connected to the pump control unit, the timer and the pressure recorder which also can operate several measuring units in parallel. Suitable software is for example LabView® by National Instruments, Munich, Germany. A complete test equipment can be delivered by High Tech Company, Ratingen/Germany, D-64293 Darmstadt.

Steps for Setting Up the Acquisition Equipment

1) Calibration of pump: before starting the experiment, the pump should be calibrated to ensure a flow rate of 75 ml per 5 seconds. If necessary, tubing should be replaced.
2) Preparation and thermal equilibration of test fluid;
3) Positioning of the cushion into the trough without folds or creases;
4) Weighing of the entire device to be tested to the nearest 0.01g on a top loading balance. Marking of the loading point onto the test specimen with a pen. Positioning and fixation (such as by suitable adhesive tape) of the test specimen to the loading unit, such that the liquid receiving surface is oriented towards the loading unit (and hence the backsheet towards the cushion), so as to have the opening aligned with the loading point of the device. The device is then positioned onto the curved loading unit without cutting the leg elastics or other elastic, if present, with the marked loading point located under the center of the tube, and attached to the loading unit by suitable attachment means, such as tape. Generally, the configuration of the device should resemble a typical in use configuration as close as possible. The device is then positioned together with the loading unit into the tester, and the electrode cables are connected.
5) The lid is closed, and fixed with screws.
6) The cushion is then inflated to the desired pressure, i.e. 2.07 kPa (0.3 psi), thereby pushing the loading unit against the lid, and thus exerting the pressure on the test specimen.
7) The end of the flexible tube is positioned such that it directs to the center of the opening, and extends about 5 cm (2 in) into the tube.
8) The liquid pump is started for the preset time (i.e. 5 seconds), and at the same time acquisition time timer.
9) Upon emptying of the Plexiglas tube the electrodes provide a signal stopping the acquisition time timer, upon which the waiting time is started at the timer for 5 minutes.
10) The loading cycle (step 7, 8 and 9) is repeated to a total of four times.

Results

Upon finishing of the above cycle, the respective acquisition rates can be calculated for each "gush" by dividing the load per gush (i.e. 75 ml) by the time in seconds required for each gush. (If the acquisition rates are getting close to the liquid delivery rates (i.e. 15 ml/sec), test conditions can be changed and respectively recorded.)

What is claimed is:

1. An absorbent article comprising an acquisition region and a waist region separate from said acquisition region characterized in that said article has a fill pattern difference of less than 30% according to Instantaneous Storage Pattern Test method defined herein.

2. An absorbent article according to claim 1, wherein said absorbent article has an fourth gush acquisition speed of at least 2 ml/s according to the Curved Acquisition Test defined herein.

3. An absorbent article according to claim 1, wherein acquired liquid is stored in at least one of said waist regions stores by a means selected from the group consisting of capillary forces and osmotic forces.

4. An absorbent article according to claim 1 said article further comprising a liquid transport member wherein said liquid transport member transports liquid from said acquisition region to said waist region.

5. An absorbent article according to claim 4, wherein said liquid transport member is substantially geometrically saturated before the intended use of the article.

6. An absorbent article according to claim 1 said article further comprising an attachment means which is unitary with said absorbent article wherein said absorbent article is attached to the lower torso of the wearer during use by means of said attachment means.

7. An absorbent article according to claim 1, wherein said article is a disposable absorbent article.

8. An absorbent article according to claim 7, wherein said article is a disposable diaper.

* * * * *